(12) United States Patent
Wellstein et al.

(10) Patent No.: US 10,351,913 B2
(45) Date of Patent: Jul. 16, 2019

(54) COMPOSITIONS AND METHODS FOR IDENTIFICATION OF RELAPSE RISK AND TREATMENT IN PATIENTS WITH COLORECTAL CANCER

(71) Applicant: Georgetown University, Washington, DC (US)

(72) Inventors: Anton Wellstein, Washington, DC (US); Narayan Shivapurkar, Potomac Falls, VA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 15/027,284

(22) PCT Filed: Oct. 7, 2014

(86) PCT No.: PCT/US2014/059454
§ 371 (c)(1),
(2) Date: Apr. 5, 2016

(87) PCT Pub. No.: WO2015/054220
PCT Pub. Date: Apr. 16, 2015

(65) Prior Publication Data
US 2016/0258024 A1    Sep. 8, 2016

Related U.S. Application Data

(60) Provisional application No. 61/887,774, filed on Oct. 7, 2013.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/118* (2013.01); *C12Q 2600/178* (2013.01)

(58) Field of Classification Search
CPC ....................................................... C12Q 1/68
See application file for complete search history.

(56) References Cited

U.S. PATENT DOCUMENTS

2008/0076674 A1 * 3/2008 Litman ............... C12Q 1/6886
506/9

FOREIGN PATENT DOCUMENTS

CN        101988060 A  *  3/2011
WO    WO 2009/111643    *  9/2011

OTHER PUBLICATIONS

Banerjee et al. (Drug Discovery Today vol. 22, No. 8, 2017: 1224-1232).*
PCT/US2014/059454, International Preliminary Report on Patentability (dated Apr. 14, 2016).
PCT/US2014/059454, International Search Report and Written Opinion (dated Dec. 22, 2014).
Tsai et al., "Clinical Significance of Micro-RNA-148a in Patients with Early Relapse of Stage II and Stage III Colorectal Cancer After Curative Resection," Transl. Res. 162(4):258-68 (2013).
Yang et al., "The Functional Significance of MicroRNA-29c in Patients with Colorectal Cancer: A Potential Circulating Biomarker for Predicting Early Relapse," PLoS One 8(6):e66842 pp. 1-9 (2013).

* cited by examiner

*Primary Examiner* — Kimberly Chong
(74) *Attorney, Agent, or Firm* — Pepper Hamilton LLP

(57) ABSTRACT

In certain aspects, the disclosure relates to methods of predicting recurrence of colorectal cancer by using a combination of microRNAs in the circulation, wherein the microRNAs are selected from the group consisting of miR-15a, miR-103, miR-148a, miR-320a, miR-451 and miR-596. In other aspects, the disclosure relates to methods of treating colorectal cancer by administering a therapeutic agent after determining an increased risk of recurrence.

23 Claims, 5 Drawing Sheets

COMPOSITIONS AND METHODS FOR IDENTIFICATION OF RELAPSE RISK AND TREATMENT IN PATIENTS WITH COLORECTAL CANCER

RELATED APPLICATIONS

This application is a United States National Stage under 35 U.S.C. § 371 of International Application No. PCT/US14/59454, filed Oct. 7, 2014 (pending), which claims the benefit of U.S. Provisional Application No. 61/887,774 filed Oct. 7, 2013, the disclosures of which are incorporated herein by reference in their entireties.

STATEMENT REGARDING FEDERALLY-SPONSORED RESEARCH OR DEVELOPMENT

This invention was made with government support under grant numbers RO1CA71508 and RO1CA108440, both awarded by the National Institutes of Health. The government has certain rights in the invention.

BACKGROUND

Colorectal cancer (CRC) is the third leading cause of cancer mortality that affects men and women equally. Worldwide it accounts for approximately one million new cancers and one-half million deaths representing 10 percent of cancer deaths [1]. Outcomes for patients with early-stage CRC are heterogeneous, with disease-specific 5-year survival rates for patients diagnosed with stage II of 72-88% and 40-71% for patients diagnosed with stage III [2]. Most patients diagnosed with stage II disease (or diagnosed with earlier stage disease) are cured by surgery alone, and thus, surgery alone is generally the standard of care for patients with early disease. For patients diagnosed with later stage disease (e.g., stage III or later), additional therapy (e.g., chemotherapy) augments the benefits of surgery and can provide survival benefits. Despite the high 5-year survival rates and use of surgery alone as the standard of care, still, approximately 1 in 4 patients diagnosed with early stage disease will suffer from recurrence. The availability of methods, such as diagnostic methods based on biomarkers, that identify patients at high risk for recurrence at the time of initial diagnosis and surgery would allow selection of those patients for closer monitoring and possibly systemic treatments ([3,4,5]; reviewed recently in [6]). Clearly, there is a need for additional approaches to diagnosing and treating colorectal cancer which is a significant public health problem.

SUMMARY OF THE INVENTION

The disclosure provides methods of predicting recurrence of colorectal cancer by using a combination of microRNAs (miRNAs or miRs). The present disclosure also provides methods of treating colorectal cancer by administering a therapeutic agent after determining a high risk of recurrence or metastasis.

In one aspect, the disclosure provides a method for predicting recurrence of early stage colorectal cancer in a patient, comprising: a) providing a biological material comprising circulating microRNAs from a patient diagnosed with stage 0, stage I or stage II colorectal cancer, b) measuring in the biological material the levels of two or more microRNAs selected from: miR-15a, miR-103, miR-148a, miR-320a, miR-451 and miR-596, and c) evaluating the measured levels; wherein the measured levels are indicative of a risk of recurrence of the cancer.

In one aspect, the disclosure provides a method for predicting recurrence of early stage colorectal cancer in a patient, comprising: a) providing a biological material comprising circulating microRNAs from a patient diagnosed with stage 0, stage I or stage II colorectal cancer, b) requesting a test comprising measuring in the biological material the levels of two or more microRNAs selected from: miR-15a, miR-103, miR-148a, miR-320a, miR-451 and miR-596, and c) evaluating the measured levels; wherein the measured levels are indicative of a risk of recurrence of the cancer.

In one aspect, the disclosure provides a method for determining a treatment regimen for a patient diagnosed with early stage colorectal cancer, comprising: a) providing a biological material comprising circulating microRNAs from a patient diagnosed with stage 0, stage I or stage II colorectal cancer, b) measuring in the biological material the levels of two or more microRNAs selected from: miR-15a, miR-103, miR-148a, miR-320a, miR-451 and miR-596, c) evaluating the measured levels, and d) providing additional cancer therapy, after surgical resection of the colorectal cancer, to the patient if the measured levels are indicative of a high risk of recurrence of the cancer.

In one aspect, the disclosure provides a method for determining a treatment regimen for a patient diagnosed with early stage colorectal cancer, comprising: a) providing a biological material comprising circulating microRNAs from a patient diagnosed with stage 0, stage I or stage II colorectal cancer, b) requesting a test comprising measuring in the biological material the levels of two or more microRNAs selected from: miR-15a, miR-103, miR-148a, miR-320a, miR-451 and miR-596, c) evaluating the measured levels; and d) providing additional cancer therapy, after surgical resection of the colorectal cancer, to the patient if the measured levels are indicative of a high risk of recurrence of the cancer.

In one aspect, the disclosure provides a method for treating early stage colorectal cancer in a patient in need thereof, comprising: a) providing a biological material comprising circulating microRNAs from a patient diagnosed with stage 0, stage I or stage II colorectal cancer, b) measuring in the biological material the levels of two or more microRNAs selected from: miR-15a, miR-103, miR-148a, miR-320a, miR-451 and miR-596, c) evaluating whether the patient is at risk of recurrence of the cancer based on the levels of the microRNAs in the biological material, and d) if the measured levels of the microRNAs in the biological material are indicative of a high risk of recurrence, (i) monitor the patient at more frequent intervals or using tests that exceed the standard of care, and/or (ii) provide additional treatment that exceeds the standard of care.

In one aspect, the disclosure provides a method for treating early stage colorectal cancer in a patient in need thereof, comprising: a) providing a biological material comprising circulating microRNAs from a patient diagnosed with stage 0, stage I or stage II colorectal cancer, b) requesting a test comprising measuring in the biological material the levels of two or more microRNAs selected from: miR-15a, miR-103, miR-148a, miR-320a, miR-451 and miR-596, c) evaluating whether the patient is at risk of recurrence of the cancer based on the levels of the micro- RNAs in the biological material, and d) if the measured levels of the microRNAs in the biological material are indicative of a high risk of recurrence, (i) monitor the patient at more frequent intervals or using tests that exceed the standard of care, and/or (ii) provide additional treatment that exceeds the standard of care.

In certain embodiments, the two or more microRNAs comprise one of miR-103 or miR-596. In certain embodiments, the two or more microRNAs comprise miR-103 and miR-596. In certain embodiments, the two or more microRNAs consist of miR-103 and miR-596. In certain embodiments, measuring in the biological material the levels of two or more microRNAs comprises measuring the levels of miR-15a, miR-103, miR-148a, miR-320a, miR-451 and miR-596. In certain embodiments, measuring in the biological material the levels of two or more microRNAs consists of measuring the levels of miR-15a, miR-103, miR-148a, miR-320a, miR-451 and miR-596. In certain embodiments, the biological material is a biological fluid. In certain embodiments, the biological fluid is selected from: blood plasma, blood serum, whole blood, urine, or feces. In certain embodiments, the biological material is obtained before the cancer is initially surgically resected. In certain embodiments, the patient is diagnosed with stage 0, I, II, III or IV colorectal cancer. In certain embodiments, the biological material is obtained after recovery from surgical resection of the cancer. In certain embodiments, steps (a) and (b) are repeated periodically if the measured levels are indicative of a low risk of recurrence of the cancer. In certain embodiments, step (a) is not performed. In certain embodiments, the microRNA levels are measured using quantitative RT-PCR. In certain embodiments, the microRNA levels are measured using hybridization methods. In certain embodiments, the microRNA levels are measured using an array. In certain embodiments, the microRNA levels are normalized to a control. In certain embodiments, the risk of recurrence of the cancer is determined by comparing the microRNA levels to a reference gene signature. In certain embodiments, the risk of recurrence of the cancer is determined by hierarchical clustering of the microRNA levels of the biological material with microRNA levels of the control biological materials from colorectal cancer patients with known recurrence outcome. In certain embodiments, the additional therapy comprises chemotherapy, radiation therapy, or therapy targeted to specific pathways known to be important in colorectal cancer or the immune system. In certain embodiments, the risk of recurrence of the cancer is predicted with at least 75% likelihood. In certain embodiments, the risk of recurrence of the cancer is predicted with at least 90% likelihood.

In one aspect, the disclosure provides a kit for measuring the levels of two or more microRNAs selected from: miR-15a, miR-103, miR-148a, miR-320a, miR-451 and miR-596, comprising reagents for specifically measuring the levels of the selected microRNAs. In certain embodiments, the two or more microRNAs comprise one of miR-103 or miR-596. In certain embodiments, the two or more microRNAs comprise miR-103 and miR-596. In certain embodiments, the two or more microRNAs consist of miR-103 and miR-596. In certain embodiments, the kit comprises reagents for specifically measuring the levels of miR-15a, miR-103, miR-148a, miR-320a, miR-451 and miR-596.

In certain embodiments, the kit comprises reagents for specifically measuring the levels of two or more microRNAs, and wherein the microRNAs consist of miR-15a, miR-103, miR-148a, miR-320a, miR-451 and miR-596. In certain embodiments, the reagents are for measuring microRNA levels using quantitative RT-PCR. In certain embodiments, the reagents are for measuring microRNA levels using hybridization methods. In certain embodiments, the reagents comprise reagents for measuring microRNA levels using an array. In certain embodiments, the microRNA levels are normalized to a control. In certain embodiments, the levels of the selected microRNAs predict the risk of recurrence of the cancer. In certain embodiments, the risk of recurrence of the cancer is determined by comparing the microRNA levels to a gene signature. In certain embodiments, the risk of recurrence of the cancer is determined by hierarchical clustering of the biological material with control biological materials from colorectal cancer patients with known recurrence outcome. In certain embodiments, the risk of recurrence of the cancer is predicted with at least 75% likelihood. In certain embodiments, the risk of recurrence of the cancer is predicted with at least 90% likelihood.

The disclosure contemplates all combinations of any of the foregoing aspects and embodiments, as well as combinations with any of the embodiments set forth in the detailed description and examples.

BRIEF DESCRIPTION OF THE DRAWINGS

The patent or application file contains at least one drawing executed in color. Copies of this patent or patent application publication with color drawings will be provided by the Office upon request and payment of the necessary fee.

For the purpose of illustrating the invention, there are depicted in the drawings certain embodiments of the disclosure. However, the disclosure is not limited to the precise arrangements and instrumentalities of the embodiments depicted in the drawings.

DETAILED DESCRIPTION OF THE INVENTION

Overview

Figure 1:
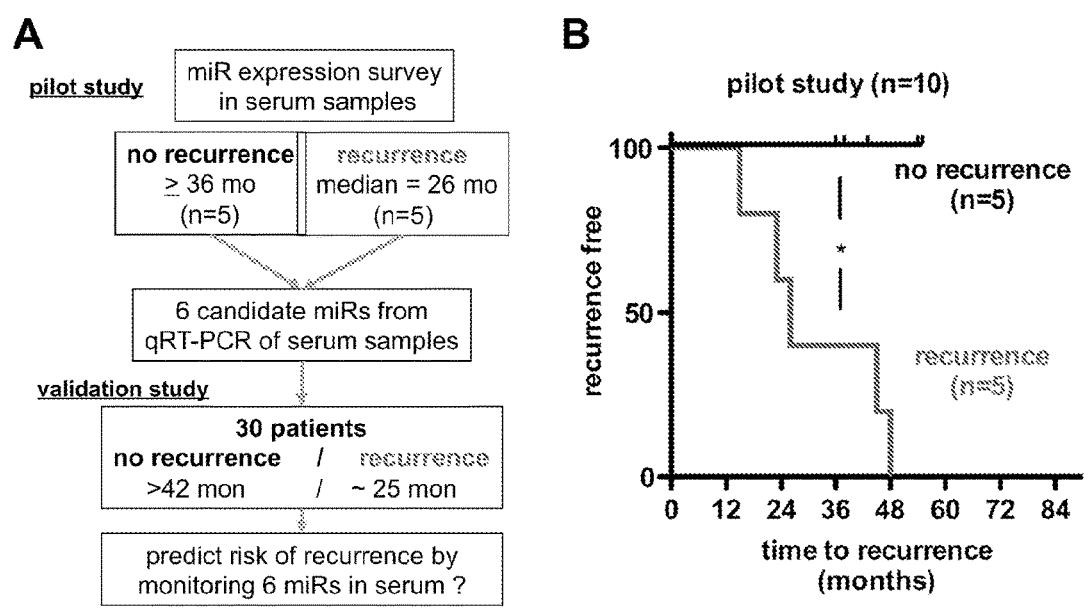
FIGS. 1A-B show the study design (A) and time-to-disease recurrence in early stage colorectal cancer patients in the pilot study (B). As depicted schematically in panel A, from a pilot study with 10 patients, candidate microRNAs (miRs) predictive of disease recurrence were identified and tested for their value in predicting disease recurrence in a validation study. Panel B shows a Kaplan-Meier plot of disease recurrence in patients in the pilot study. Patients with disease recurrence (n=5) vs no recurrence (n=5): Chi square 5.47, p=0.0193; median time-to-recurrence=26 months. The Gehan-Breslow-Wilcoxon algorithms were used.

The disclosure provides methods and kits for evaluating whether a patient diagnosed with an early stage colorectal cancer, a cancer which typically has a high five-year cure rate following treatment with surgery alone (e.g., a low risk of recurrence; a low risk of metastasis), is at risk for recurrence following this initial surgery. Without being bound by theory, since patients diagnosed with early stage colorectal cancer have a high five-year cure rate, their risk of recurrence within 5 years is generally considered low, and thus, therapy (e.g., chemotherapy or radiation therapy) adjuvant to surgery is not the standard of care. However, cancer does recur within five years in a subset of patients diagnosed with early stage colorectal cancer. It may be that the higher risk subset is actually misdiagnosed with early stage colorectal cancer because of the limitations of current clinical diagnostic methods. Regardless of the reason for recurrence, the ability to identify patients at high risk of recurrence provides the opportunity to provide those patients with additional treatment options and/or increased monitoring.

The present disclosure provides methods and kits to identify patients who, based on levels of certain miRNAs in the circulation at the time of their initial diagnosis and/or surgery, are at risk of recurrence within the first five years (e.g., identifying the patients who fall into the subset of patients whose cancer will recur; identifying patients whose risk of recurrence is high, relative to the average risk predicted across the population of patients diagnosed with early stage colorectal cancer). If those patients are identified early, such as at the time of initial surgery, they can be offered adjuvant therapy or increased monitoring to help prevent or delay recurrence, or to ensure that any recurrence is detected as early as possible. Accordingly the present disclosure provides improved methods for treating patients with colorectal cancer, such as patients diagnosed with early stage colorectal cancer.

Definitions

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

"Clinical parameters" encompasses all non-sample or non-analyte biomarkers of subject health status or other characteristics, such as, without limitation, age (Age), ethnicity (RACE), gender (Sex), or family history (FamHX).

"Circulating tumor cell" ("CTC") is a tumor cell which is shed from the primary tumor upon metastasis, and enters the circulation. The number of circulating tumor cells in peripheral blood is associated with prognosis in patients with metastatic colorectal cancer.

"FN" is false negative, which for a test to identify high risk of recurring colorectal cancer means classifying a subject at high risk of recurring colorectal cancer incorrectly as low risk.

"FP" is false positive, which for a test to identify high risk of recurring colorectal cancer means classifying a low risk subject incorrectly as high risk.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use in combining the predictive value of one microRNA with another are linear and non-linear equations and statistical classification analyses to determine the relationship between levels of microRNAs detected in a subject sample and the subject's risk of recurrence or metastatic disease. In panel and combination construction, of particular interest are structural and synactic statistical classification algorithms, and methods of risk index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, among others. Other techniques may be used in survival and time to event hazard analysis, including Cox, Weibull, Kaplan-Meier and Greenwood models well known to those of skill in the art. Many of these techniques are useful either combined with a microRNA selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art. A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

In some embodiments, for diagnostic (or prognostic) interventions of the disclosure, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

"Measuring" or "measurement," or alternatively "detecting" or "detection" or "assaying," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's non-analyte clinical parameters.

"Negative predictive value" or "NPV" is calculated by TN/(TN+FN) or the true negative fraction of all negative test results. It also is inherently impacted by the prevalence of the disease and pre-test probability of the population intended to be tested.

See, e.g., O'Marcaigh et al., *Clin. Ped.* (1993), which discusses specificity, sensitivity, and positive and negative predictive values of a test, e.g., a clinical diagnostic test.

Often, for binary disease state classification approaches using a continuous diagnostic test measurement, the sensitivity and specificity is summarized by Receiver Operating Characteristics (ROC) curves according to Pepe et al, *Am. J. Epidemiol* (2004), and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4$^{th}$ edition 1996, W.B. Saunders Company, pages 192-199; and Zweig et al., *Clin. Chem.*, (1992). An alternative approach using likelihood functions, odds ratios, information theory, predictive values, calibration (including goodness-of-fit), and reclassification measurements is summarized according to Cook, Circulation (2007).

Finally, hazard ratios and absolute and relative risk ratios within subject cohorts defined by a test are a further measurement of clinical accuracy and utility. Multiple methods are frequently used to defining abnormal or disease values, including reference limits, discrimination limits, and risk thresholds.

"Analytical accuracy" refers to the reproducibility and predictability of the measurement process itself, and may be summarized in such measurements as coefficients of variation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC, time to result, shelf life, etc. as relevant.

"Positive predictive value" or "PPV" is calculated by TP/(TP+FP) or the true positive fraction of all positive test results. It is inherently impacted by the prevalence of the disease and pre-test probability of the population intended to be tested.

"Risk" in the context of the present disclosure, relates to the probability that an event will occur over a specific time period, as in the conversion to metastatic events, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no-conversion.

"Risk evaluation," or "evaluation of risk" in the context of the present disclosure encompasses making a prediction of the probability, odds, or likelihood that an event or disease state may occur, the rate of occurrence of the event or conversion from one disease state to another, i.e., from a primary tumor to metastatic colorectal cancer or to one at risk of developing a metastatic, or from at risk of a primary metastatic event to a more secondary metastatic event. Risk evaluation can also comprise prediction of future clinical parameters, traditional laboratory risk factor values, or other indices of cancer, either in absolute or relative terms in reference to a previously measured population. The methods of the present disclosure may be used to make continuous or categorical measurements of the risk of metastatic colorectal cancer thus diagnosing and defining the risk spectrum of a category of subjects defined as being at risk for colorectal cancer. In the categorical scenario, the disclosure can be used to discriminate between subject cohorts at higher risk for colorectal cancers and lower risk. Such differing use may require different microRNA combinations and individualized panels, mathematical algorithms, and/or cut-off points, but be subject to the same aforementioned measurements of accuracy and performance for the respective intended use.

A "biological material" in the context of the present disclosure is a biological material isolated or otherwise obtained, directly or indirectly, from a subject that comprises circulating microRNAs and can include, by way of example and not limitation, a tissue sample, whole blood, serum, plasma, lymphatic fluid, ascites fluid, interstitial fluid (also known as "extracellular fluid" and encompasses the fluid found in spaces between cells, including, inter alia, gingival cevicular fluid), bone marrow, cerebrospinal fluid (CSF), saliva, mucous, sputum, sweat, urine, feces, or any other secretion, excretion, or other bodily fluids. In certain embodiments, the analysis can be done with a small amount (e.g., <1 ml) of biological material. It should be understood that the biological material used for analysis may be directly obtained from the subject (e.g., miRNA is measured in the very same sample obtained) or the sample obtained from the subject may be further processed such that a portion of that sample is used for further analysis (e.g., a blood sample is obtained from the patient and processed, and miRNA is measured in serum). In either case, the disclosure provides methods of measuring miRNA in a biological material comprising circulating miRNAs and obtained from a patient. In certain embodiments, only mature miR makes it into the circulation because the pre-miR is processed in the nucleus and exported to the cytosol and from there only mature miR makes it into the circulation.

A "gene signature" is an expression pattern of more than one microRNA.

"Sensitivity" is calculated by TP/(TP+FN).

"Specificity" is calculated by TN/(TN+FP).

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

A "subject" or "patient" in the context of the present disclosure is preferably a human patient. In certain embodiments, the subject is a mammal. The mammal can be a non-human primate, mouse, rat, dog, cat, horse, or cow, but are not limited to these examples. Mammals other than humans can be advantageously used as subjects that represent animal models of tumor metastasis. A subject can be male or female. A subject can be one who has been previously diagnosed or identified as having primary tumor or a colorectal cancer, and optionally has already undergone, or is undergoing, a therapeutic intervention for the tumor. Alternatively, a subject can also be one who has not been previously diagnosed as having metastatic colorectal cancer. For example, a subject can be one who exhibits one or more risk factors for metastatic colorectal cancer or colorectal cancer recurrence.

"TN" is true negative, which for a test to identify high risk of recurring colorectal cancer means classifying a subject at low risk of recurring colorectal cancer correctly.

"TP" is true positive, which for a test to identify high risk of recurring colorectal cancer means classifying a subject at high risk of recurring colorectal cancer correctly.

"Traditional laboratory risk factors" correspond to biomarkers isolated or derived from subject samples and which are currently evaluated in the clinical laboratory and used in traditional global risk assessment algorithms. Traditional laboratory risk factors for tumor metastasis include for example depth of invasion, vessel density, proliferative index, etc. Other traditional laboratory risk factors for tumor metastasis are known to those skilled in the art.

Methods and Uses of the Disclosure

The present disclosure provides methods to identify colorectal cancer patients who, based on the levels of two or more of miR-15a, miR-103, miR-148a, miR-320a, miR-451 and miR-596 in the circulation at the time of their initial surgery to remove the primary tumor, are at risk of recurrence relative to the average risk predicted across the patient population, such as relative to the average risk predicted across patients diagnosed with early stage colorectal cancer (e.g., stage 0, stage I, and/or stage II). In certain embodiments, patients determined to be at high risk of recurrence can be offered adjuvant therapy or increased monitoring to help prevent or delay recurrence, or to ensure that any recurrence is detected as early as possible.

In this method, in certain embodiments, one obtains a biological material from the patient (e.g., a patient diagnosed with stage 0, stage 1, or stage II colorectal cancer), and measures the levels of two or more of miR-15a, miR-103, miR-148a, miR-320a, miR-451 and miR-596 in the sample (e.g., in all or any portion of the sample, such as in serum or plasma prepared from a blood sample taken from the patient), wherein the measured levels are indicative of the prognosis of the cancer patient (e.g., indicative of the risk that the subject will have a recurrence of their colorectal cancer). The microRNAs of the disclosure include two or more of miR-15a, miR-103, miR-148a, miR-320a, miR-451 and miR-596. In other words, in certain embodiments, the method comprises measuring, in a sample, circulating levels of two or more mature miRNAs selected from miR-15a, miR-103, miR-148a, miR-320a, miR-451 and miR-596. Obtaining a biological material includes obtaining fresh biological material, such as biological material taken at a given time for the purpose of this analysis. Obtaining a biological material also includes using previously obtained biological material taken at another point during patient care for this or for other purposes, or using archived patient material. Biological material may be freshly obtained or previously obtained, and where previously obtained may have been stored prior to use (e.g., at room temperature, refrigerated, or frozen).

In certain embodiments, the biological material comprises circulating microRNAs. Exemplary biological materials include, but are not limited to, whole blood, serum, plasma, urine, feces, cerebrospinal fluid, ascites, and the like. In certain embodiments, regardless of the biological material harvested from the patient, the sample is processed such that miRNA levels are measured in a portion of the sample. In certain embodiments, miRNA levels are measured in portion of the sample that is substantially cell free. In certain embodiments, miRNAs are measured in serum or plasma, such as serum or plasma prepared from a blood sample drawn from a patient. Regardless of whether the biological material harvested from the patient is used directly or further processed before use, either case is an example of measuring miRNA in a biological material from a patient.

One or more, preferably two or more of the listed microRNAs may be measured in the practice of the present disclosure. For example, 2, 3, 4, 5 or 6, microRNAs may be measured. In certain embodiments, the microRNAs measured comprise one of miR-103 or miR-596 (and optionally comprise measuring 1, 2, 3, 4, or 5 additional miRNAs). In certain embodiments, the microRNAs measured comprise miR-103 and miR-596 (and optionally comprise measuring 1, 2, 3, or 4 additional miRNAs). In certain embodiments, the microRNAs measured consist of miR-103 and miR-596. In certain embodiments, the microRNAs measured comprise at least 2, at least 3, at least 4, at least 5, or 6 of the following: miR-15a, miR-103, miR-148a, miR-320a, miR-451 and miR-596. In certain embodiments, the microRNAs measured consist of miR-15a, miR-103, miR-148a, miR-320a, miR-451 and miR-596. In some embodiments, at least one of the selected microRNAs has a statistically significant increase in the measured levels compared to the average initially diagnosed patient and at least one of the selected microRNAs has a statistically significant decrease in the measured levels compared to the average initially diagnosed patient. In some embodiments, additional biomarkers are measured or additional patient parameters are considered in combination with the microRNAs.

In certain embodiments, a patient is at high or increased risk of recurrence if miR-15a, miR-103, miR-148a, miR-320a, and/or miR-451 are at lower levels than in the average initially diagnosed patient or a low risk control index. In certain embodiments, a patient is at high or increased risk of recurrence if miR-596 is at higher levels than in the average initially diagnosed patient or a low risk control index.

In some embodiments, the prognosis may be that the patient is at a low risk of having metastatic cancer or recurrence of cancer. In other embodiments, the prognosis may be that the patient is at a high risk of having metastatic cancer or recurrence of cancer. In certain embodiments, low risk may be about 99% likelihood of 5-year survival or not having recurrence. In certain embodiments, low risk may be about 95, 90, 85, 80, 75, 70, 65, 60, or 55% likelihood of 5-year survival or not having recurrence. In certain embodiments, high risk may be about 1% likelihood of 5-year survival or not having recurrence. In certain embodiments, high risk may be about 5, 10, 15, 20, 25, 30, 35, 40, or 45% likelihood of 5-year survival or not having recurrence.

In some embodiments, a high or an increased risk over average for the initial diagnosis of cancer recurrence or developing metastatic cancer in the patient is determined by measuring a statistically significant alteration in the levels of the selected microRNAs in the sample. Alternatively, an increased risk of cancer recurrence or developing metastatic colorectal cancer in the patient is determined by comparing the levels of the selected microRNAs to a reference value. In some embodiments, the reference value is an index.

The disclosure also provides a method for analyzing a biological material from a cancer patient. In this method, one obtains the biological material from the patient and measures the levels of two or more of miR-15a, miR-103, miR-148a, miR-320a, miR-451 and miR-596 in the sample.

In certain embodiments, the measurements are done using a kit. In certain embodiments, the measurements are outsourced to a laboratory.

This disclosure additionally provides a method for identifying a cancer patient in need of adjuvant therapy after surgical resection of the primary colorectal tumor. In this method, one obtains a biological material from the patient, measures the levels of two or more of miR-15a, miR-103, miR-148a, miR-320a, miR-451 and miR-596 in the sample, wherein the measured levels indicate that the patient is in need of adjuvant therapy. In certain embodiments, the patient would normally not be given adjuvant therapy or additional therapy is optional based on the standard of care of the initial stage of diagnosis. In certain embodiments, the microRNA analysis indicates that the patient is at high risk for recurrence or metastasis.

For any of the foregoing, the disclosure contemplates that patients identified as at risk for recurrence may be given or offered adjuvant treatment, in additional to surgical resection which is the standard of care. For example, the adjuvant therapy may be selected from the group consisting of radiation therapy, chemotherapy, immunotherapy, hormone therapy, and targeted therapy. In some embodiments, the patient has been subjected to a standard of care therapy. In some embodiments, the additional therapy comprises chemotherapy or radiation therapy or therapy targeted to specific pathways known to be important in colorectal cancer or the immune system. Therapeutics may comprise small molecules, recombinant proteins, monoclonal antibodies or other chemical or biological entities used in colorectal cancer treatment. In certain embodiments, the circulating miRs identified may contribute to the process by impacting tumor cell survival, tumor stromal interactions, angiogenesis or inflammatory cell responses to the occult metastases and may be targeted.

In some embodiments, chemotherapeutic agents that are suitable for the methods of the disclosure include, but are not limited to, EGFR inhibitors, immunomodulators, DNA-alkylating agents, anti-tumor antibiotic agents, anti-metabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial and exotoxic agents. Examples of suitable agents for the compositions of the present disclosure include, but are not limited to, cytidine arabinoside, methotrexate, vincristine, etoposide (VP-16), doxorubicin (adriamycin), cisplatin (CDDP), dexamethasone, arglabin, cyclophosphamide, sarcolysin, methylnitrosourea, fluorouracil, 5-fluorouracil (5FU), vinblastine, camptothecin, actinomycin-D, mitomycin C, hydrogen peroxide, oxaliplatin, irinotecan, topotecan, leucovorin, carmustine, streptozocin, CPT-11, taxol, tamoxifen, dacarbazine, rituximab, daunorubicin, 1-beta-D-arabinofuranosylcytosine, imatinib, fludarabine, docetaxel, FOLFOX4, Avastin® (bevacizumab), Erbitux® (cetuximab), and Vectibix® (panitumumab). FOLFOX (leucovorin, 5-FU, oxaliplatin (Eloxatin)), FOLFIRI (leucovorin, 5-FU, and irinotecan (Camptosar)), CapeOX (capecitabine (Xeloda) and oxaliplatin), 5-FU and leucovorin, with or without bevacizumab, Capecitabine, with or without bevacizumab, FOLFOXIRI (leucovorin, 5-FU, oxaliplatin, and irinotecan), Irinotecan, with or without cetuximab, and Regorafenib (Stivarga).

This disclosure also provides a further method for treating a colorectal cancer patient. In this method, one measures the levels of two or more of miR-15a, miR-103, miR-148a, miR-320a, miR-451 and miR-596 in a biological material from the patient, and treats or offers to treat the patient with adjuvant therapy if the measured levels indicate that the patient is at a high risk of having metastatic cancer or a recurrence of cancer. In some embodiments, the adjuvant therapy is the standard of care for metastatic or recurrent colorectal cancer. In some embodiments, the adjuvant therapy is a radiation or a chemotherapeutic as described above. In some embodiments, the adjuvant therapy is an experimental therapy. In certain embodiments, the patient is monitored more than the standard of care. In certain embodiments, the patient is monitored weekly, every two weeks, monthly, every 2, 3, 4, 5, or 6 months, or yearly. In certain embodiments, the patient is offered adjuvant treatment that exceeds the standard of care for patients diagnosed with stage 0, I, or II. In certain embodiments, the microRNAs measured comprise miR-103 and miR-596 (and optionally comprise measuring 1, 2, 3, or 4 additional miRNAs). In certain embodiments, the microRNAs measured consist of miR-103 and miR-596. In certain embodiments, the microRNAs measured comprise at least 2, at least 3, at least 4, at least 5, or 6 of the following: miR-15a, miR-103, miR-148a, miR-320a, miR-451 and miR-596. In certain embodiments, the microRNAs measured consist of miR-15a, miR-103, miR-148a, miR-320a, miR-451 and miR-596. In certain embodiments, the biological material comprises circulating microRNAs.

This disclosure additionally provides a method for monitoring the progression of colorectal cancer in a patient. In this method, one obtains a biological material from the patient; and measures the levels of two or more of miR-15a, miR-103, miR-148a, miR-320a, miR-451 and miR-596 in the sample, and wherein the measured levels are indicative of the progression of the tumor in the patient. In some embodiments, a statistically significant alteration in the measured levels between the biological material taken form the patient at two different time points is indicative of the progression of the tumor in the patient. In some embodiments, the progression of a tumor in a patient is measured by detecting the levels of the selected microRNAs in a first sample from the patient taken at a first period of time, detecting the levels of the selected microRNAs in a second sample from the patient taken at a second period of time and then comparing the levels of the selected microRNAs to a reference value. In some aspects, the first sample is taken from the patient prior to being treated for the tumor and the second sample is taken from the patient after being treated for the tumor.

The disclosure also provides a method for monitoring the effectiveness of treatment or selecting a treatment regimen for a recurrent or metastatic colorectal cancer in a patient by measuring the levels of two or more of miR-15a, miR-103, miR-148a, miR-320a, miR-451 and miR-596 in a first sample from the patient taken at a first period of time and optionally measuring the level of the selected microRNAs in a second sample from the patient taken at a second period of time. The levels of the selected microRNAs detected at the first period of time are compared to the levels detected at the second period of time or alternatively a reference value. The effectiveness of treatment is monitored by a change in the measured levels of the selected microRNAs from the patient.

The progression of metastatic colorectal cancer, or effectiveness of a cancer treatment regimen can be monitored by detecting a microRNA in an effective number (which may be two or more of miR-15a, miR-103, miR-148a, miR-320a, miR-451 and miR-596) of blood samples obtained from a subject over time and comparing the amount of microRNAs detected. For example, a first blood sample can be obtained prior to the subject receiving treatment and one or more subsequent samples are taken after or during treatment of the subject. The cancer is considered to be progressive (or, alternatively, the treatment does not prevent progression) if the amount of microRNA changes over time relative to the reference value, whereas the cancer is not progressive if the amount of microRNAs remains constant over time (relative to the reference population, or "constant" as used herein). The term "constant" as used in the context of the present disclosure is construed to include changes over time with respect to the reference value.

For example, the methods of the disclosure can be used to discriminate the aggressiveness/and or accessing the stage of the tumor (e.g. Stage 0, I, II, III or IV). This will allow patients to be stratified into high or low risk groups and treated accordingly.

The present disclosure further provides a method for screening for changes in marker expression associated with metastatic colorectal cancer, by determining the amount (which may be two or more) of microRNAs selected from miR-15a, miR-103, miR-148a, miR-320a, miR-451 and miR-596 in a subject-derived sample, comparing the amounts of the microRNAs in a reference sample, and identifying alterations in amounts in the subject sample compared to the reference sample.

The present disclosure further provides a method of treating a patient with colorectal cancer by identifying a patient with a tumor where an effective number (e.g., two or more) of miR-15a, miR-103, miR-148a, miR-320a, miR-451 and miR-596 are altered in a statistically significant manner as measured in a sample from the tumor, and treating the patient with a therapeutic regimen that prevents or reduces tumor metastasis.

Additionally the disclosure provides a method of selecting a colorectal cancer patient in need of adjuvant treatment by assessing the risk of metastasis or recurrence in the patient by measuring an effective number of microRNAs where a statistically significant alteration in two or more of miR-15a, miR-103, miR-148a, miR-320a, miR-451 and miR-596 in a tumor sample from the patient indicates that the patient is in need of adjuvant treatment.

In certain embodiments, if the reference sample, e.g., a control sample, is from a subject that does not have metastatic colorectal cancer, or if the reference sample reflects a value that is relative to a person that has a high likelihood of rapid progression to metastatic colorectal cancer, a similarity in the amount of the microRNA in the test sample and the reference sample indicates that the treatment is efficacious. However, a difference in the amount of the microRNA in the test sample and the reference sample indicates a less favorable clinical outcome or prognosis.

By "efficacious", it is meant that the treatment leads to improvement in the health of the patient. Assessment of the risk factors disclosed herein can be achieved using standard clinical protocols. Efficacy can be determined in association with any known method for diagnosing, identifying, or treating colorectal cancer.

Also provided by the present disclosure is a method for treating one or more subjects at risk for developing a colorectal cancer by detecting the presence of altered amounts of an effective number (e.g., two or more) of miR-15a, miR-103, miR-148a, miR-320a, miR-451 and miR-596 present in a sample from the one or more subjects; and treating the one or more subjects with one or more cancer-modulating drugs until altered amounts of the microRNAs return to a baseline value measured in one or more subjects at low risk for developing a metastatic disease, or alternatively, in subjects who do not exhibit any of the traditional risk factors for metastatic disease.

Also provided by the present disclosure is a method for treating one or more subjects having colorectal cancer by detecting the presence of altered levels of an effective number of two or more of miR-15a, miR-103, miR-148a, miR-320a, miR-451 and miR-596 present in a sample from the one or more subjects; and treating the one or more subjects with one or more cancer-modulating drugs until altered amounts of the microRNAs return to a baseline value measured in one or more subjects at low risk for developing colorectal cancer.

Also provided by the present disclosure is a method for evaluating changes in the risk of developing metastatic colorectal cancer in a subject diagnosed with cancer, by detecting an effective number of microRNAs selected from miR-15a, miR-103, miR-148a, miR-320a, miR-451 and miR-596 in a first sample from the subject at a first period of time, detecting the amounts of the microRNAs in a second sample from the subject at a second period of time, and comparing the amounts of the microRNAs detected at the first and second periods of time.

In certain embodiments, the methods of the disclosure are used with a kit for measuring the levels of two or more of miR-15a, miR-103, miR-148a, miR-320a, miR-451 and miR-596. The kit comprises reagents for specifically measuring the levels of the selected microRNAs. In some embodiments, the reagents are nucleic acid molecules. In these embodiments, the nucleic acid molecules are PCR primers or hybridizing probes. In alternative embodiments, the reagents are antibodies or fragments thereof, oligonucleotides, or aptamers. In certain embodiments, substantially only circulating miRNAs in the sample are measured (e.g., such as in serum samples).

In some embodiments, at least one of the selected microRNAs has a statistically significant increase in the measured levels and at least one of the selected microRNAs has a statistically significant decrease in the measured levels.

The levels of the selected microRNAs may be measured electrophoretically or immunochemically. For example, the levels of the selected microRNAs are detected by radioimmunoassay, immunofluorescence assay or by an enzyme-linked immunosorbent assay. Optionally, the microRNAs are detected using non-invasive imaging technology. In certain embodiments, substantially only circulating miRNAs in the sample are measured (e.g., such as in serum samples).

In some embodiments, the RNA transcript levels of the selected microRNAs are measured. In certain embodiments, the RNA transcript levels may be determined by microarray, quantitative RT-PCR, sequencing, nCounter® multiparameter quantitative detection assay (NanoString), branched DNA assay (e.g., Panomics QuantiGene® Plex technology), or quantitative nuclease protection assay (e.g., Highthroughput Genomics qNPA™). nCounter® system is developed by NanoString Technology. It is based on direct multiplexed measurement of gene expression and capable of providing high levels of precision and sensitivity (<1 copy per cell) (see 72.5.117.165/applications/technology/). In particular, the nCounter® assay uses molecular "barcodes" and single molecule imaging to detect and count hundreds of unique transcripts in a single reaction. Panomics QuantiGene® Plex technology can also be used to assess the RNA expression of microRNAs in this disclosure. The QuantiGene® platform is based on the branched DNA technology, a sandwich nucleic acid hybridization assay that provides a unique approach for RNA detection and quantification by amplifying the reporter signal rather than the sequence (Flagella et al., *Analytical Biochemistry* (2006)). It can reliably measure quantitatively RNA expression in fresh, frozen or formalin-fixed, paraffin-embedded (FFPE) tissue homogenates (Knudsen et al., *Journal of Molecular Diagnostics* (2008)). In certain embodiments, substantially only circulating miRNAs in the sample are measured (e.g., such as in serum samples).

In some embodiments, the levels of the microRNAs may be measured separately. Alternatively, the levels of the microRNAs may be measured in a multiplex reaction. In certain embodiments, measuring miRNAs comprises measuring circulating miRNAs in a sample. In certain embodiments, miRNAs are measured in a sample that is substantially cell free or has a significantly reduced number of cells relative to an initial tissue sample. In certain embodiments, substantially only circulating miRNAs in the sample are measured (e.g., such as in serum samples).

In some embodiments, the biological material is a solid tissue sample, a bodily fluid sample, or circulating tumor cells. In some embodiments, the bodily fluid sample may be blood, plasma, urine, saliva, lymph fluid, cerebrospinal fluid (CSF), synovial fluid, cystic fluid, ascites, pleural effusion, interstitial fluid, or ocular fluid. In some embodiments, the solid tissue sample may be a formalin-fixed paraffin embedded tissue sample, a snap-frozen tissue sample, an ethanol-fixed tissue sample, a tissue sample fixed with an organic solvent, a tissue sample fixed with plastic or epoxy, a cross-linked tissue sample, surgically removed tumor tissue, or a biopsy sample (e.g., a core biopsy, an excisional tissue biopsy, or an incisional tissue biopsy). In some embodiments, the tissue sample is a cancerous tissue sample. In certain embodiments, the biological material is blood, and measuring miRNA comprises measuring levels in plasma or serum prepared from the blood.

In some embodiments, at least one standard parameter associated with the cancer is measured in addition to the measured levels of the selected microRNAs. The at least one standard parameter may be, for example, tumor stage, tumor grade, tumor size, tumor visual characteristics, tumor location, tumor growth, lymph node status, tumor thickness (Breslow score), ulceration, or age of onset.

Also included in the disclosure is a reference expression profile containing a pattern of marker levels of an effective number of two or more of miR-15a, miR-103, miR-148a, miR-320a, miR-451 and miR-596 associated with high risk of recurrence or metastatic colorectal cancer. Also included is a machine readable media containing one or more reference expression profiles and optionally, additional test results and subject information. In a further aspect the disclosure provides a microRNA panel containing one or more microRNAs that are indicative of a physiological or biochemical pathway associated with predicted metastasis or the progression of a tumor.

The methods disclosed herein may be used with subjects at risk for developing metastatic colorectal cancer or having a colorectal cancer recurrence. For example, although early stage colorectal cancer has a high 5 year cure rate (e.g., a relatively low rate of recurrence and/or progression to metastatic disease within 5 years), a subset of patients progress to recurrence or metastatic disease within 5 years. The methods of the present disclosure are useful for identifying, from amongst patients with early stage colorectal cancer, those patients that are at high risk of recurrence or progression to metastatic disease (e.g., identifying those patients at high risk of being in the subset of patients whose cancer recurs or progresses within 5 years). Because early stage colorectal cancer has such a high 5 year survival rate, the standard of care typically comprises surgery to resect the cancer, but without adjuvant radiation or chemotherapy. With the methods of the present disclosure, patients at high risk of recurrence or progression to metastatic disease are identified and those patients can then be offered additional treatment options. For example, these patients can be offered increased monitoring or adjuvant therapy following surgery but prior to any recurrence.

The methods of the present disclosure can also be used to monitor or select a treatment regimen for a subject who has a primary tumor or metastatic colorectal cancer, and to screen subjects who have not been previously diagnosed as having metastatic colorectal cancer, such as subjects who exhibit risk factors for metastasis or reoccurrence. Preferably, the methods of the present disclosure are used to identify and/or diagnose subjects who are asymptomatic for metastatic colorectal cancer. "Asymptomatic" means not exhibiting the traditional signs and symptoms.

The methods of the present disclosure may also used to identify and/or diagnose subjects already at higher risk of developing metastatic colorectal cancer or colorectal cancer recurrence based on solely on the traditional risk factors.

In certain embodiments, a subject having a high risk of recurrence or having metastatic colorectal cancer can be identified by measuring the amounts (including the presence or absence) of an effective number (which can be two or more) of microRNAs selected from miR-15a, miR-103, miR-148a, miR-320a, miR-451 and miR-596 in a subject-derived sample and the amounts are then compared to a reference value. Alterations in the amounts and patterns of expression of the microRNAs in the subject sample compared to the reference value are then identified.

A reference value can be relative to a number or value derived from population studies, including without limitation, such subjects having the same stage colorectal cancer, subjects having the same or similar age range, subjects in the same or similar ethnic group, subjects having family histories of cancer, or relative to the starting sample of a subject undergoing treatment for a cancer. Such reference values can be derived from statistical analyses and/or risk prediction data of populations obtained from mathematical algorithms and computed indices of cancer metastasis. Reference microRNA indices can also be constructed and used using algorithms and other methods of statistical and structural classification.

In one embodiment of the present disclosure, the reference value is the amount of two or more of miR-15a, miR-103, miR-148a, miR-320a, miR-451 and miR-596 in a control sample derived from one or more subjects who are not at risk or at low risk for developing metastatic colorectal cancer or for recurrence. In another embodiment of the present disclosure, the reference value is the amount of two or more of miR-15a, miR-103, miR-148a, miR-320a, miR-451 and miR-596 in a control sample derived from one or more subjects who are asymptomatic and/or lack traditional risk factors for metastatic colorectal cancer. In a further embodiment, such subjects are monitored and/or periodically retested for a diagnostically relevant period of time ("longitudinal studies") following such test to verify continued absence of metastatic colorectal cancer (disease or event free survival). Such period of time may be one year, two years, two to five years, five years, five to ten years, ten years, or ten or more years from the initial testing date for determination of the reference value. Furthermore, retrospective measurement of microRNAs in properly banked historical subject samples may be used in establishing these reference values, thus shortening the study time required.

A reference value can also comprise the amounts of microRNAs derived from subjects who show an improvement in metastatic or recurrence risk factors as a result of treatments and/or therapies for the cancer. A reference value can also comprise the amounts of microRNAs derived from subjects who have confirmed disease by known invasive or non-invasive techniques, or are at high risk for developing colorectal cancer, or who have suffered from metastatic or recurrent colorectal cancer.

In another embodiment, the reference value is an index value or a baseline value. An index value or baseline value is a composite sample of an effective number of two or more of miR-15a, miR-103, miR-148a, miR-320a, miR-451 and miR-596 from one or more subjects who do not have colorectal cancer, or subjects who are asymptomatic for metastatic cancer. A baseline value can also comprise the amounts of two or more of miR-15a, miR-103, miR-148a, miR-320a, miR-451 and miR-596 in a sample derived from a subject who has shown an improvement in colorectal cancer risk factors as a result of cancer treatments or therapies. In this embodiment, to make comparisons to the subject-derived sample, the amounts of microRNAs are similarly calculated and compared to the index value. Optionally, subjects identified as having colorectal cancer, being at increased risk of developing metastatic colorectal cancer or colorectal cancer recurrence are chosen to receive a therapeutic regimen to slow the progression the cancer, or decrease or prevent the risk of developing metastatic or recurrent colorectal cancer.

Diagnostic and Prognostic Indications

The risk of developing metastatic colorectal cancer or colorectal cancer recurrence can be detected by measuring an effective number of microRNAs selected from two or more of miR-15a, miR-103, miR-148a, miR-320a, miR-451 and miR-596 in a biological material (e.g., a subject derived sample), and comparing the amounts to reference or index values, often utilizing mathematical algorithms or formula in order to combine information from results of multiple individual microRNAs and from non-analyte clinical parameters into a single measurement or index. Subjects identified as having an increased risk of metastatic colorectal cancer or colorectal cancer recurrence can optionally be selected to receive treatment regimens, such as administration of prophylactic or therapeutic compounds discussed above to prevent or delay the onset of metastatic colorectal cancer or colorectal cancer recurrence.

The amount of the microRNAs can be measured in a test sample and compared to the "normal control level," e.g., low risk of colorectal cancer recurrence, utilizing techniques such as reference limits, discrimination limits, or risk defining thresholds to define cutoff points and abnormal values. The "normal control level" means the level of one or more microRNAs or combined microRNA indices typically found in a subject at low risk of colorectal cancer recurrence. Such normal control level and cutoff points may vary based on whether a microRNA is used alone or in a formula combining with other microRNAs into an index. Alternatively, the normal control level can be a database of microRNA patterns from previously tested subjects who did not develop a colorectal cancer or did not develop metastatic or recurrent colorectal cancer over a clinically relevant time horizon.

The present disclosure may be used to make continuous or categorical measurements of the risk of conversion to metastatic colorectal cancer or colorectal cancer recurrence thus diagnosing and defining the risk spectrum of a category of subjects defined as at risk for having a metastatic or recurrent event. In the categorical scenario, the methods of the present disclosure can be used to discriminate between normal and disease subject cohorts. In other embodiments, the present disclosure may be used so as to discriminate those at risk for having a metastatic or recurrent event from those having more rapidly progressing (or alternatively those with a shorter probable time horizon to a metastatic or recurrent event) to a metastatic event from those more slowly progressing (or with a longer time horizon to a metastatic event), or those having metastatic cancer from normal. Such differing use may require different microRNA combinations in individual panel, mathematical algorithm, and/or cut-off points, but be subject to the same aforementioned measurements of accuracy and other performance metrics relevant for the intended use.

Identifying the subject at risk of having a metastatic or recurrent event enables the selection and initiation of various therapeutic interventions or treatment regimens in order to delay, reduce or prevent that subject's conversion to a metastatic disease state. Levels of an effective number of microRNAs also allows for the course of treatment of a metastatic disease or metastatic event to be monitored. In this method, a biological sample can be provided from a subject undergoing treatment regimens, e.g., drug treatments, for colorectal cancer. If desired, biological samples are obtained from the subject at various time points before, during, or after treatment.

The present disclosure can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like cancer or metastatic events, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein.

A machine-readable storage medium can comprise a data storage material encoded with machine readable data or data arrays which, when using a machine programmed with instructions for using said data, is capable of use for a variety of purposes, such as, without limitation, subject information relating to metastatic disease risk factors over time or in response drug therapies. Measurements of effective numbers of the biomarkers of the disclosure and/or the resulting evaluation of risk from those biomarkers can implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system of the disclosure may also be considered to be implemented as a computer-readable storage medium, configured with a computer program, where the storage medium so configured causes a computer to operate in a specific and predefined manner to perform various functions described herein.

Levels of an effective number of microRNAs can then be determined and compared to a reference value, e.g. a control subject or population whose metastatic state is known or an index value or baseline value. The reference sample or index value or baseline value may be taken or derived from one or more subjects who have been exposed to the treatment, or may be taken or derived from one or more subjects who are at low risk of developing cancer or a metastatic event, or may be taken or derived from subjects who have shown improvements in as a result of exposure to treatment. Alternatively, the reference sample or index value or baseline value may be taken or derived from one or more subjects who have not been exposed to the treatment. For example, samples may be collected from subjects who have received initial treatment for caner or a metastatic event and subsequent treatment for cancer or a metastatic event to monitor the progress of the treatment. A reference value can also comprise a value derived from risk prediction algorithms or computed indices from population studies such as those disclosed herein.

The microRNAs of the present disclosure can thus be used to generate a "reference microRNA profile" of those subjects who do not have cancer or are not at risk of having a metastatic event, and would not be expected to develop cancer or a metastatic event. The microRNAs disclosed herein can also be used to generate a "subject microRNA profile" taken from subjects who have cancer or are at risk for having a metastatic event. The subject microRNA profiles can be compared to a reference microRNA profile to diagnose or identify subjects at risk for developing cancer or a metastatic event, to monitor the progression of disease, as well as the rate of progression of disease, and to monitor the effectiveness of treatment modalities. The reference and subject microRNA profiles of the present disclosure can be contained in a machine-readable medium, such as but not limited to, analog tapes like those readable by a VCR, CD-ROM, DVD-ROM, USB flash media, among others. Such machine-readable media can also contain additional test results, such as, without limitation, measurements of clinical parameters and traditional laboratory risk factors. Alternatively or additionally, the machine-readable media can also comprise subject information such as medical history and any relevant family history. The machine-readable media can also contain information relating to other disease-risk algorithms and computed indices such as those described herein.

Differences in the genetic makeup of subjects can result in differences in their relative abilities to metabolize various drugs, which may modulate the symptoms or risk factors of cancer or metastatic events. Subjects that have cancer, or at risk for developing cancer, a recurrent cancer or a metastatic cancer can vary in age, ethnicity, and other parameters. Accordingly, use of the microRNAs disclosed herein, both alone and together in combination with known genetic factors for drug metabolism, allow for a pre-determined level of predictability that a putative therapeutic or prophylactic to be tested in a selected subject will be suitable for treating or preventing cancer or a metastatic event in the subject.

The aforementioned methods of the disclosure can be used to evaluate or monitor the progression and/or improvement of subjects who have been diagnosed with a cancer, and who have undergone surgical interventions.

Performance and Accuracy Measures

The performance and thus absolute and relative clinical usefulness of the disclosure may be assessed in multiple ways, as noted above. Amongst the various assessments of performance, the disclosure is intended to provide accuracy in clinical diagnosis and prognosis. The accuracy of a diagnostic or prognostic test, assay, or method for distinguishing between subjects at risk for recurrence of colorectal cancer or a metastatic event, is based on whether the subjects have, a "significant alteration" (e.g., statistically significant, diagnostically significant) in the levels of a microRNA. By "effective number" it is meant that the measurement of an appropriate number of microRNAs (which may be two or more) to produce a "significant alteration," (e.g. level of expression of a microRNA) that is different than the predetermined cut-off point (or threshold value) for that microRNA(s) and therefore indicates that the subject is at risk of recurrence or having a metastatic event for which the microRNA(s) is a determinant. The difference in the level of microRNA between low risk and high risk is preferably statistically significant. As noted below, and without any limitation of the disclosure, achieving statistical significance, and thus the preferred analytical, diagnostic, and clinical accuracy, often requires that combinations of at least two microRNAs be used together in panels and combined with mathematical algorithms in order to achieve a statistically significant microRNA index.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points.

In certain embodiments, the methods predict the risk of recurrence of colorectal cancer, metastatic cancer or response to therapy with at least 75% accuracy, more preferably 80%, 85%, 90%, 95%, 97%, 98%, 99% or greater accuracy.

A health economic utility function is an yet another means of measuring the performance and clinical value of a given test, consisting of weighting the potential categorical test outcomes based on actual measures of clinical and economic value for each. Health economic performance is closely related to accuracy, as a health economic utility function specifically assigns an economic value for the benefits of correct classification and the costs of misclassification of tested subjects. As a performance measure, it is not unusual to require a test to achieve a level of performance which results in an increase in health economic value per test (prior to testing costs) in excess of the target price of the test.

In general, alternative methods of determining diagnostic accuracy are commonly used for continuous measures, when a disease category or risk category (such as those at risk for recurrence or having a metastatic event) has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, Calif.).

In general, by defining the degree of diagnostic accuracy, i.e., cut points on a ROC curve, defining an acceptable AUC value, and determining the acceptable ranges in relative concentration of what constitutes an effective number of two or more of miR-15a, miR-103, miR-148a, miR-320a, miR-451 and miR-596 allows for one of skill in the art to use the microRNAs to identify, diagnose, or prognose subjects with a pre-determined level of predictability and performance.

Construction of microRNA Panels

Groupings of microRNAs can be included in "panels." A "panel" within the context of the present disclosure means a group of biomarkers (whether they are microRNAs, clinical parameters, or traditional laboratory risk factors) that includes more than one microRNA. A panel can also comprise additional biomarkers, e.g., clinical parameters, traditional laboratory risk factors, known to be present or associated with cancer or cancer metastasis, in combination with a selected group of two or more of miR-15a, miR-103, miR-148a, miR-320a, miR-451 and miR-596.

As noted above, many of the individual microRNAs, clinical parameters, and traditional laboratory risk factors listed, when used alone and not as a member of a multi-biomarker panel of microRNAs, have little or no clinical use in reliably distinguishing individual subjects at risk for recurrence or having a metastatic event, and thus cannot reliably be used alone in classifying any subject between those states. Even where there are statistically significant differences in their mean measurements in each of these populations, as commonly occurs in studies which are sufficiently powered, such biomarkers may remain limited in their applicability to an individual subject, and contribute little to diagnostic or prognostic predictions for that subject. A common measure of statistical significance is the p-value, which indicates the probability that an observation has arisen by chance alone; preferably, such p-values are 0.05 or less, representing a 5% or less chance that the observation of interest arose by chance. Such p-values depend significantly on the power of the study performed.

Despite this individual microRNA performance, and the general performance of formulas combining only the traditional clinical parameters and few traditional laboratory risk factors, the present inventors have noted that certain specific combinations of two or more microRNAs can also be used as multi-biomarker panels comprising combinations of microRNAs and that such information can be combined and made clinically useful through the use of various formulae, including statistical classification algorithms and others, combining and in many cases extending the performance characteristics of the combination beyond that of the individual microRNAs. These specific combinations show an acceptable level of diagnostic accuracy, and, when sufficient information from multiple microRNAs is combined in a trained formula, often reliably achieve a high level of diagnostic accuracy transportable from one population to another.

The general concept of how two less specific or lower performing microRNAs are combined into novel and more useful combinations for the intended indications, is a key aspect of the disclosure. Multiple biomarkers can often yield better performance than the individual components when proper mathematical and clinical algorithms are used; this is often evident in both sensitivity and specificity, and results in a greater AUC. Secondly, there is often novel unperceived information in the existing biomarkers, as such was necessary in order to achieve through the new formula an improved level of sensitivity or specificity. This hidden information may hold true even for biomarkers which are generally regarded to have suboptimal clinical performance on their own. In fact, the suboptimal performance in terms of high false positive rates on a single biomarker measured alone may very well be an indicator that some important additional information is contained within the biomarker results—information which would not be elucidated absent the combination with a second biomarker and a mathematical formula.

Several statistical and modeling algorithms known in the art can be used to both assist in microRNA selection choices and optimize the algorithms combining these choices. Statistical tools such as factor and cross-biomarker correlation/ covariance analyses allow more rationale approaches to panel construction. Mathematical clustering and classification tree showing the Euclidean standardized distance between the microRNAs can be advantageously used. Pathway informed seeding of such statistical classification techniques also may be employed, as may rational approaches based on the selection of individual microRNAs based on their participation across in particular pathways or physiological functions.

Ultimately, formula such as statistical classification algorithms can be directly used to both select microRNAs and to generate and train the optimal formula necessary to combine the results from multiple microRNAs into a single index. Often, techniques such as forward (from zero potential explanatory parameters) and backwards selection (from all available potential explanatory parameters) are used, and information criteria, such as AIC or BIC, are used to quantify the tradeoff between the performance and diagnostic accuracy of the panel and the number of microRNAs used. The position of the individual microRNA on a forward or backwards selected panel can be closely related to its provision of incremental information content for the algorithm, so the order of contribution is highly dependent on the other constituent microRNAs in the panel.

Construction of Clinical Algorithms

Any formula may be used to combine microRNA results of two or more of miR-15a, miR-103, miR-148a, miR-320a, miR-451 and miR-596 into indices useful in the practice of the disclosure. As indicated above, and without limitation, such indices may indicate, among the various other indications, the probability, likelihood, absolute or relative risk, time to or rate of conversion from one to another disease states, or make predictions of future biomarker measurements of metastatic disease. This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population. The specifics of the formula itself may commonly be derived from microRNA results in the relevant training population. Amongst other uses, such formula may be intended to map the feature space derived from one or more microRNA inputs to a set of subject classes (e.g. useful in predicting class membership of subjects as low or high risk for having a metastatic event, or recurring colorectal cancer), to derive an estimation of a probability function of risk using a Bayesian approach (e.g. the risk of cancer or a metastatic event), or to estimate the class-conditional probabilities, then use Bayes' rule to produce the class probability function as in the previous case.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic. In certain embodiments, a Principal Component Analysis (PCA) is used. In certain embodiments, PCA may be used with continuous methods adding new subjects.

Eigengene-based Linear Discriminant Analysis (ELDA) is a feature selection technique developed by Shen et al. (2006). The formula selects features (e.g. biomarkers) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual microRNA measurement into more valuable forms of information, prior to their presentation to the predictive formula. Most notably, normalization of biomarker results, using either common mathematical transformations such as logarithmic or logistic functions, as normal or other distribution positions, in reference to a population's mean values, etc. are all well known to those skilled in the art. Of particular interest are a set of normalizations based on Clinical Parameters such as age, gender, race, or sex, where specific formula are used solely on subjects within a class or continuously combining a Clinical Parameter as an input. In other cases, analyte-based biomarkers can be combined into calculated variables which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean biomarker parameter values, according to the technique outlined in D'Agostino et al, *JAMA* (2001), or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al, 2004 on the limitations of odds ratios; Cook, N. R., 2007 relating to ROC curves. Finally, the numeric result of a classifier formula itself may be transformed post-processing by its reference to an actual clinical population and study results and observed endpoints, in order to calibrate to absolute risk and provide confidence intervals for varying numeric results of the classifier or risk formula. An example of this is the presentation of absolute risk, and confidence intervals for that risk, derived using an actual clinical study, chosen with reference to the output of the recurrence score formula in the Oncotype Dx product of Genomic Health, Inc. (Redwood City, Calif.). A further modification is to adjust for smaller sub-populations of the study based on the output of the classifier or risk formula and defined and selected by their Clinical Parameters, such as age or sex.

Combination with Clinical Parameters and Traditional Laboratory Risk Factors

Any of the aforementioned Clinical Parameters may be used in the practice of the disclosure as a microRNA input to a formula or as a pre-selection criteria defining a relevant population to be measured using a particular microRNA panel and formula. As noted above, Clinical Parameters may also be useful in the biomarker normalization and pre-processing, or in microRNA selection, panel construction, formula type selection and derivation, and formula result post-processing. A similar approach can be taken with the Traditional Laboratory Risk Factors, as either an input to a formula or as a pre-selection criterium.

Measurement of microRNAs

The actual measurement of levels or amounts of the microRNAs can be determined using any method known in the art. For example, at the nucleic acid level, Northern and Southern hybridization analysis, as well as ribonuclease protection assays using probes which specifically recognize one or more of these sequences can be used to determine gene expression. Alternatively, amounts of microRNAs can be measured using reverse-transcription-based PCR assays (RT-PCR), e.g., using primers specific for the differentially expressed sequence of genes or by branch-chain RNA amplification and detection methods by Panomics, Inc. The primers can be 22, 21, 20, 19, 18, 17, 16, 15, 14, 13, 12, 11, 10, 9, 8, 7, 6 or less nucleotides in length.

Using sequence information provided by the database entries for the microRNA sequences, expression of the microRNA sequences can be detected (if present) and measured using techniques well known to one of ordinary skill in the art. For example, sequences within the sequence database entries corresponding to microRNA sequences, or within the sequences disclosed herein, can be used to construct probes for detecting microRNA sequences in, e.g., Northern blot hybridization analyses or methods which specifically, and, preferably, quantitatively amplify specific nucleic acid sequences. As another example, the sequences can be used to construct primers for specifically amplifying the microRNA sequences in, e.g., amplification-based detection methods such as reverse-transcription based polymerase chain reaction (RT-PCR). When alterations in gene expression are associated with gene amplification, deletion, polymorphisms, and mutations, sequence comparisons in test and reference populations can be made by comparing relative amounts of the examined DNA sequences in the test and reference cell populations.

Expression of the microRNAs disclosed herein can be measured using any method known in the art. For example, Northern hybridization analysis using probes which specifically recognize one or more of these sequences can be used to determine gene expression. Alternatively, expression can be measured using reverse-transcription-based PCR assays (RT-PCR), e.g., using primers specific for the differentially expressed sequences. RNA can also be quantified using, for example, other target amplification methods (e.g., TMA, SDA, NASBA), or signal amplification methods (e.g., bDNA), and the like. In certain embodiments, the miRNAs measured are circulating miRNAs.

Kits

The disclosure also includes a microRNA-detection reagent, e.g., nucleic acids that specifically identify two or more of miR-15a, miR-103, miR-148a, miR-320a, miR-451 and miR-596 by having homologous nucleic acid sequences, such as oligonucleotide sequences, complementary to a portion of the microRNAs or antibodies to the microRNAs packaged together in the form of a kit. The oligonucleotides can be fragments of the microRNA genes. For example the oligonucleotides can be 22, 21, 20, 19, 18, 17, 16, 15, 14, 13, 12, 11, 10, 9, 8, 7, 6 or less nucleotides in length. The kit may contain in separate containers a nucleic acid or antibody (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a Northern hybridization or a sandwich ELISA as known in the art. In certain embodiments, substantially only circulating miRNAs in the sample are measured (e.g., such as in serum samples).

For example, microRNA detection reagents can be immobilized on a solid matrix such as a porous strip to form at least one microRNA detection site. The measurement or detection region of the porous strip may include a plurality of sites containing a nucleic acid. A test strip may also contain sites for negative and/or positive controls. Alternatively, control sites can be located on a separate strip from the test strip. Optionally, the different detection sites may contain different amounts of immobilized nucleic acids, e.g., a higher amount in the first detection site and lesser amounts in subsequent sites. Upon the addition of test sample, the number of sites displaying a detectable signal provides a quantitative indication of the amount of microRNAs present in the sample. The detection sites may be configured in any suitably detectable shape and are typically in the shape of a bar or dot spanning the width of a test strip.

Alternatively, the kit contains a nucleic acid substrate array comprising one or more nucleic acid sequences. The nucleic acids on the array specifically identify two or more nucleic acid sequences represented by miR-15a, miR-103, miR-148a, miR-320a, miR-451 and miR-596 can be identified by virtue of binding to the array. The substrate array can be on, e.g., a solid substrate, e.g., a "chip" as described in U.S. Pat. No. 5,744,305. Alternatively, the substrate array can be a solution array, e.g., xMAP (Luminex, Austin, Tex.), Cyvera (Illumina, San Diego, Calif.), CellCard (Vitra Bioscience, Mountain View, Calif.) and Quantum Dots' Mosaic (Invitrogen, Carlsbad, Calif.). In certain embodiments, substantially only circulating miRNAs in the sample are measured (e.g., such as in serum samples).

Suitable sources for antibodies for the detection of microRNAs include commercially available sources such as, for example, Abazyme, Abnova, Affinity Biologicals, Antibody-Shop, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, nucleic acid probes, e.g., oligonucleotides, aptamers, siRNAs, antisense oligonucleotides, against any of miR-15a, miR-103, miR-148a, miR-320a, miR-451 and miR-596.

Kits of the disclosure may also contain additional suitable reagents, and such reagents may be in one or more containers. In certain embodiments, the kit contains reference samples and/or controls used to calibrate or read the assay. In certain embodiments, the kit contains instructions for use.

EXEMPLIFICATION

The disclosure now being generally described, it will be more readily understood by reference to the following examples, which are included merely for purposes of illustration of certain aspects and embodiments of the present disclosure, and are not intended to limit the disclosure. For example, the particular constructs and experimental design disclosed herein represent exemplary tools and methods for validating proper function. As such, it will be readily apparent that any of the disclosed specific constructs and experimental plan can be substituted within the scope of the present disclosure.

Example 1: Materials and Methods for Examples

The collection and use of biospecimens was approved by the Institutional Review Board (IRB) of Georgetown University under Protocol #2007-345, most recently on Oct. 24, 2012. All patients signed a consent form permitting the use of donated tissue and body fluid samples. The consent forms and their content was reviewed and approved by the IRB.

Serum samples (<1 ml) were processed after preparation from blood samples and after removal of personal identifiers. miR isolation was described previously [18]. In brief, serum samples were mixed at a ratio of 1:10 with Qiazol lysis reagent and vortexed. The lysate was extracted with $CHCl_3$ and the aqueous phase was further processed for total RNA using the miRNeasy Mini kit (Qiagen, Valencia, Calif.) and enriched for miR using the RT2 qPCR-Grade miR Isolation Kit, MA-01 (SABiosciences). Quantitative RT-PCR was performed as described [33]. Primers for quantitative RT-PCR to specific miRs are commercially available.

PCA and hierarchical clustering were performed based on the mean centered and scaled miR expression levels. The clustering methods used XLSTAT (Addinsoft Inc.) within Excel (Microsoft Inc.) on OSX 10.7.5. These methods allow for the calculation of significance between the hierarchical clusters and derive p-values using Fisher's exact test. Prism 5.0 (Graphpad) software was used for other tests and display of the data.

Figure 2:
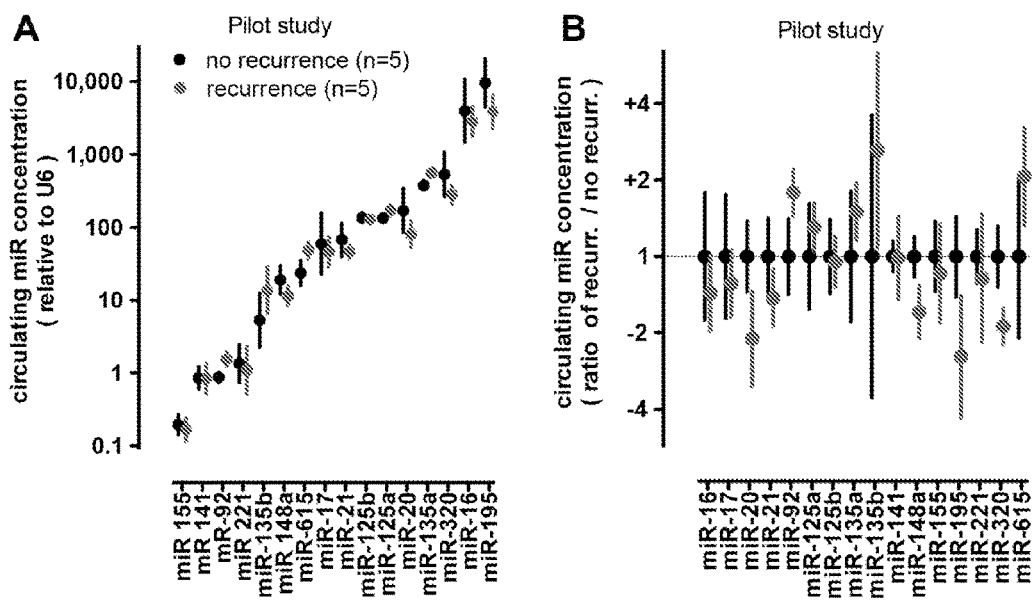
FIGS. 2A-B show miR expression levels in serum samples from patients with or without recurrence of early stage colorectal cancer (Pilot Study; Candidate miRNA approach). Circulating levels of 16 miRs indicated on the x-axis that had been published as differentially expressed between colorectal cancer and non-malignant colon tissues were analyzed [21,34,35]. Pre-surgery serum samples were from patients in the pilot study. Patients had been followed for disease recurrence and the respective data are in FIG. 1B. Panel A, Concentration of circulating miRs (relative to U6). Note the log-scale covers a range of 100,000-fold. Panel B, ratio of expression between patient groups. Although miR-20, miR-195 and miR-320 showed a ≥2-fold downregulation, and miR-135b and miR-615 a ≥2-fold upregulation in serum from patients with disease recurrence, neither of the comparisons reached statistical significance by ANOVA (p>0.05).

Example 2: Circulating MicroRNA Expression Comparison Using a Candidate Gene Approach To measure miRs in the circulation, we established quantitative RT-PCR [33] as a detection method with a dynamic range up to $10^6$-fold for miRs in serum samples [18]. As an initial approach, we picked a panel of sixteen miRs that had been shown to be differentially expressed between colorectal cancer and normal colon tissues [21,34,35]. We initially ran a pilot study and analyzed a set of serum samples obtained from early stage colorectal cancer patients that remained disease-free (n=5) or had disease recurrence (n=5) within an average of 26 months (<0.05 vs. no recurrence; FIG. 1A,B). FIG. 2A shows the approximately 100,000-fold concentration range of the sixteen circulating miRs analyzed in the pilot study. We observed the expected trends of the respective up- or down-regulation in some of the selected miRs (i.e. miR-20, miR-135b, miR-195, miR-320, miR-615). However, the differences were not statistically significant (FIG. 2B). It is noteworthy that miR-320 was one of two miRs that showed a downregulation in tissues that was correlated with poor recurrence-free survival [21]. Here, miR-320 in the circulation was approximately two-fold lower in patients with disease recurrence, though that downregulation was not statistically significant (FIG. 2B). The expression of miR-498, the other miR from the study in Ref [21], was detected only at very low levels in the circulation and thus not suitable for the analysis.

Figure 3:
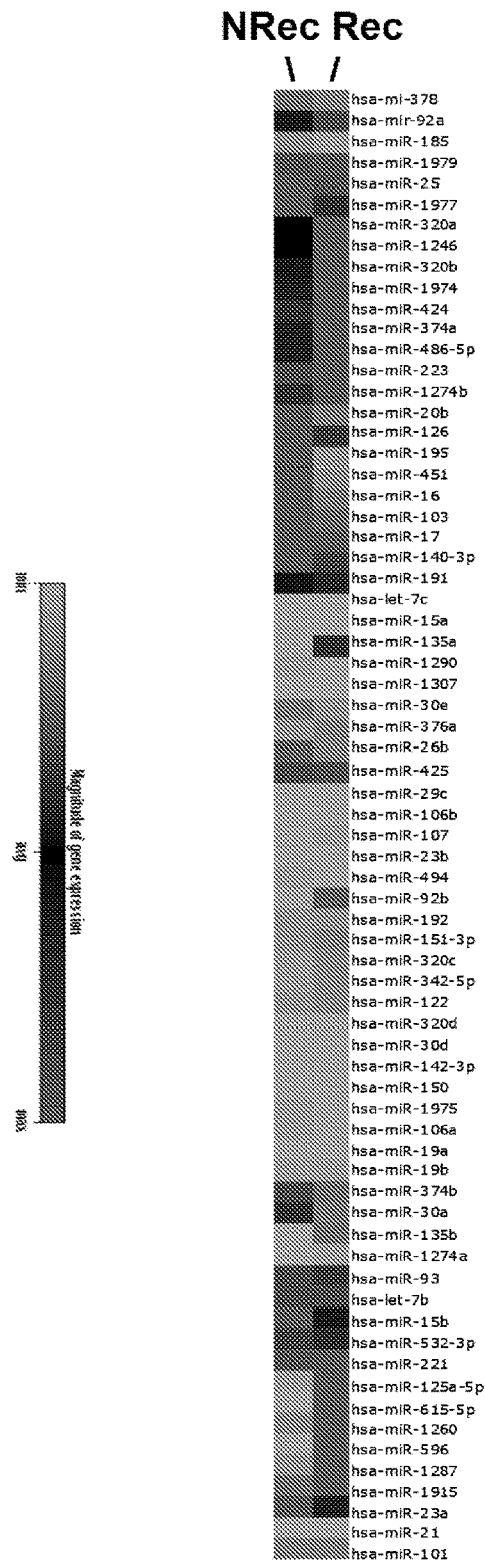
FIG. 3 shows miRNA expression levels in serum samples from two patients with (Rec) or without (Nrec) 5-year recurrence of early stage colorectal cancer. Heat map of genome-wide microRNA expression analysis. Two patients were selected from the pilot study (see FIGS. 1 and 2). The miRNA expression analysis was carried out for 760 miRNAs using qPCR-based expression analysis. Data filtration and analysis were conducted and the 70 miRs that show the biggest differential expression are represented in the heat map.

Example 3: Circulating MicroRNA Expression Comparison Using an Unbiased, Genome-Wide Analysis From the above pilot study we selected two patient samples from the recurrence-free (NRec) and recurrence (Rec) group for an unbiased genome-wide miR analysis. We picked patients from the above pilot study whose samples had shown the most differential expression of candidate miRs. We reasoned that a comparison within such a sample pair might offer a greater chance of picking up recurrence-specific miRs. We analyzed this pair of patient samples using SYBR Green qPCR based genome-wide miR expression arrays for 760 miRs set up in our laboratory, using commercially available reagents (SBI, Mountain view CA). The respective result for the top 70 miRs is shown in FIG. 3 as a heatmap. For an independent validation study we selected from this panel six miRs that met two criteria: (1) sufficient levels of expression in serum samples, i.e. RT-PCR Ct values ≤32 and (2) differential expression (>3-fold up- or down-regulation) of a given miR comparing Rec and NRec samples.

Example 4: Validation of Circulating MicroRNA Expression Patterns as a Predictor of Disease Recurrence To evaluate whether the six circulating miRs selected in Example 3 can predict disease recurrence in low-risk patients, we used a separate, independent group of thirty patients with early stage colorectal cancer with known outcomes. Fifteen of these patients had disease recurrence within an average of 25 months whereas the other fifteen remained recurrence-free. The clinical characteristics of patients in this validation set at the time of their initial diagnosis is provided in Table 1. At the time of diagnosis the two groups of patients without and with disease recurrence showed no significant differences with respect to age, gender, tumor size, tumor stage, location of their primary lesion or histopathology (Table 1). All patients had node-negative disease and more than twelve lymph nodes examined. Only one patient (in the non-recurrence group) was a T4, all others were T1 to T3 tumors and thus with a low known risk of recurrence.

Figure 4:
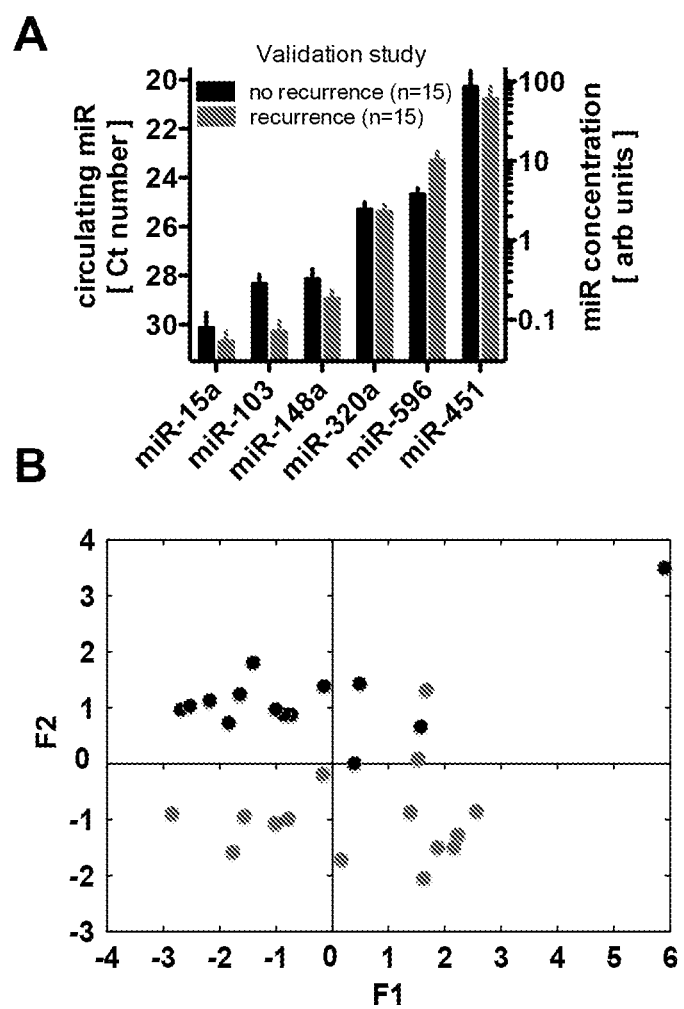
FIGS. 4A-B show miR expression levels in serum samples from patients with or without recurrence of early stage colorectal cancer. Validation study for six miRs identified in the Pilot study. Patient characteristics are provided in Table 1. Six miRs were derived from the pilot study. A, Expression levels based on the cycle threshold (Ct) values of the qRT-PCR (left axis) and the miR concentration calculated (right axis). B, Principal Component Analysis of the data with the two groups shown in black and red symbols respectively.

Expression of the six miRs was measured by qRT-PCR and the resulting data are shown as raw Ct values as well as a concentration range in FIG. 4A (left and right axes respectively). The concentration of the six selected miRs in the circulation covers a range of approximately 1,000 fold, and thus a 100-fold narrower range than the miRs monitored in the pilot study (compare FIGS. 4A and 2A). A correlation analysis of the data showed a strong correlation of the expression levels of miR-15a, miR-148a, miR-320a and miR-451 (r=0.746 to 0.897; p<0.0001) whereas levels of miR-103 and miR-596 were not correlated with the levels of the other miRs. A Principal Component Analysis (PCA) of the expression level data of the 6 miR set showed a distinct grouping of patients with and without recurrence (FIG. 4B) suggesting that the panel of miRs may distinguish the different recurrence risks of patients.

TABLE 1

Patient characteristics in the validation study

| parameter | recurrence (n = 15) | no recurrence (n = 15) | P-value (across groups) |
|---|---|---|---|
| age (years) | 69.5 ± 2.4 | 62.5 ± 3.1 | P > 0.05 |
| gender (female/male) | 3/12 | 9/6 | P > 0.05 |
| tumor size (cm) | 3.8 ± 0.4 | 3.9 ± 0.3 cm | P > 0.05 |
| stage: T1/T2/T3/T4 | 2/2/11/0 | 1/7/6/1 | P > 0.05 |
| lymph nodes (positive out of median number examined [range]) | 0/16 [12 to 54] | 0/24 [13 to 58] | P > 0.05 |
| location (ascending & transverse/sigmoid/rectal) | 5/5/5 | 4/8/3 | P > 0.05 |
| histopathology (moderately/poorly differentiated) | 12/3 | 14/1 | P > 0.05 |
| leukocytes (cells/nl) | 7.8 ± 1.9 | 6.0 ± 0.3 | P > 0.05 |
| CEA (ng/ml) [median; 5%-95% C.I.] | 2.8 [1.0-63.8] | 1.6 [0.7-4.8] | P > 0.05 |

Example 5: Blinded Hierarchical Clustering Analysis

Figure 5:
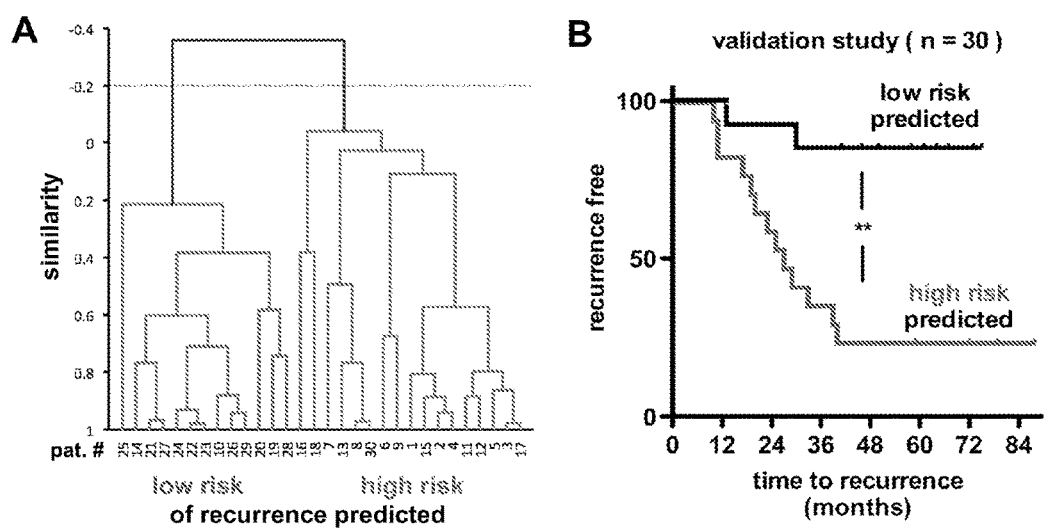
FIGS. 5A-B show disease recurrence in patients relative to their risk predicted from the serum levels of miRs. Panel A depicts hierarchical clustering of patients from the validation study into low and high risk groups based on six serum miR levels. The analysis resulted in a separation into two groups. B, Kaplan-Meier plot of survival of patients predicted to have high and low risk of disease recurrence. The comparison resulted in P=0.0026, Hazard Ratio 5.4 (1.9 to 15.095% CI). In panel A patients with disease recurrence are #1 to #15 and without recurrence: #16 to #30.

A blinded hierarchical clustering analysis of the six miRs [18] (FIG. 5A) showed a significant subsetting into two distinct groups. Thirteen of fifteen patients with disease recurrence and eleven of fifteen patients that were recurrence-free were correctly classified by the six miRs in the blood samples collected before their initial surgery (p=0.0025; odds ratio=17.9; rel. risk=5.5, 95% CI=1.5 to 20.7). A Kaplan-Meier analysis of the times to disease recurrence in the patients assigned to high or low risk by the hierarchical clustering showed a significantly different outcome between the two groups (P=0.0026, FIG. 5B). Thus, the six miRs selected here can be used to predict the risk of disease recurrence of early stage, low-risk colorectal cancer by the analysis of a blood sample collected at the time of the initial diagnosis.

When analyzing the miRs one-by-one rather than in a multivariate analysis, two miRs were found differentially expressed in the circulation, i.e. miR-103 (downregulated) and miR-596 (upregulated). miR-103 was significantly down-regulated (p=0.038) in blood samples from patients with disease recurrence compared to recurrence-free patients (FIG. 4A). In contrast, miR-596 was significantly up-regulated (p=0.0012) in blood samples from patients with disease recurrence.

Example 6: Clinical Prognosis and Treatment of Colorectal Cancer in Patients

Patients diagnosed with stage 0, I or II colorectal cancer will have serum samples obtained before the surgical resection of the primary tumor. The panel of six microRNAs described in the previous examples will be used to predict the risk of cancer recurrence as described in Example 5.

If the analysis of the microRNAs predicts a high risk of recurrent cancer in a patient, that patient will be treated with adjuvant therapy as determined by consultation of the physician and patient. Patients predicted to be at low risk will not undergo further treatment, as per the standard of care for patients diagnosed with stage 0, stage I, or stage II colorectal cancer.

It is expected that the high risk patients will benefit from the additional treatment by reducing the chance of recurrence. It is also expected that low risk patients will benefit from not undergoing unnecessary treatment.

TABLE 2

Sequences

| | |
|---|---|
| hsa-miR-15a | UAGCAGCACAUAAUGGUUUGUG (SEQ ID NO: 1) |
| hsa-miR-103 | AGCAGCAUUGUACAGGGCUAUGA (SEQ ID NO: 2) |
| hsa-miR-148a | UCAGUGCACUACAGAACUUUGU (SEQ ID NO: 3) |
| hsa-miR-320a | AAAAGCUGGGUUGAGAGGGCGA (SEQ ID NO: 4) |
| hsa-miR-451 | AAACCGUUACCAUUACUGAGUU (SEQ ID NO: 5) |
| hsa-miR-596 | AAGCCUGCCCGGCUCCUCGGG (SEQ ID NO: 6) |

REFERENCES

1. Siegel R, Naishadham D, Jemal A (2012) Cancer statistics, 2012. CA: a cancer journal for clinicians 62: 10-29.
2. Gunderson L L, Jessup J M, Sargent D J, Greene F L, Stewart A K (2010) Revised TN categorization for colorectal cancer based on national survival outcomes data. J Clin Oncol 28: 264-271.
3. Poste G (2011) Bring on the biomarkers. Nature 469: 156-157.
4. Henry N L, Hayes D F (2012) Cancer biomarkers. Molecular Oncology 6: 140-146.
5. Poste G, Carbone D P, Parkinson D R, Verweij J, Hewitt S M, et al. (2012) Leveling the playing field: bringing development of biomarkers and molecular diagnostics up to the standards for drug development. Clin Cancer Res 18: 1515-1523.
6. Kerr D J, Shi Y (2013) Biological markers: Tailoring treatment and trials to prognosis. Nat Rev Clin Oncol AOP Jun. 11, 2013: 1-2.
7. Bartel D P (2004) MicroRNAs: genomics, biogenesis, mechanism, and function. Cell 116: 281-297.
8. Ventura A, Jacks T (2009) MicroRNAs and cancer: short RNAs go a long way. Cell 136: 586-591.
9. Visone R, Croce C M (2009) MiRNAs and cancer. Am J Pathol 174: 1131-1138.
10. Cummins J M, He Y, Leary R J, Pagliarini R, Diaz L A, et al. (2006) The colorectal microRNAome. Proc Natl Acad Sci USA 103: 3687-3692.
11. Roldo C, Missiaglia E, Hagan J P, Falconi M, Capelli P, et al. (2006) MicroRNA expression abnormalities in pancreatic endocrine and acinar tumors are associated with distinctive pathologic features and clinical behavior. J Clin Oncol 24: 4677-4684.
12. Buchholz M, Kestler H A, Bauer A, Bock W, Rau B, et al. (2005) Specialized DNA arrays for the differentiation of pancreatic tumors. Clin Cancer Res 11: 8048-8054.
13. Bloomston M, Frankel W L, Petrocca F, Volinia S, Alder H, et al. (2007) MicroRNA expression patterns to differentiate pancreatic adenocarcinoma from normal pancreas and chronic pancreatitis. JAMA 297: 1901-1908.
14. Calin G A, Croce C M (2006) MicroRNA signatures in human cancers. Nat Rev Cancer 6: 857-866.
15. Walther A, Johnstone E, Swanton C, Midgley R, Tomlinson I, et al. (2009) Genetic prognostic and predictive markers in colorectal cancer. Nat Rev Cancer 9: 489-499.
16. Volinia S, Calin G A, Liu C-G, Ambs S, Cimmino A, et al. (2006) A microRNA expression signature of human solid tumors defines cancer gene targets. Proc Natl Acad Sci USA 103: 2257-2261.
17. Shimono Y, Zabala M, Cho R W, Lobo N, Dalerba P, et al. (2009) Downregulation of miRNA-200c links breast cancer stem cells with normal stem cells. Cell 138: 592-603.
18. LaConti J J, Shivapurkar N, Preet A, Deslattes Mays A, Peran I, et al. (2011) Tissue and Serum microRNAs in the Kras Transgenic Animal Model and in Patients with Pancreatic Cancer. PLoS ONE 6: e20687.
19. Lu J, Getz G, Miska E, Alvarez-Saavedra E, Lamb J, et al. (2005) MicroRNA expression profiles classify human cancers. Nature 435: 834-838.
20. Rosenfeld N, Aharonov R, Meiri E, Rosenwald S, Spector Y, et al. (2008) MicroRNAs accurately identify cancer tissue origin. Nat Biotechnol 26: 462-469.
21. Schepeler T, Reinert J T, Ostenfeld M S, Christensen L L, Silahtaroglu A N, et al. (2008) Diagnostic and prognostic microRNAs in stage II colorectal cancer. Cancer Res 68: 6416-6424.
22. Mitchell P S, Parkin R K, Kroh E M, Fritz B R, Wyman S K, et al. (2008) Circulating microRNAs as stable blood-based markers for cancer detection. Proc Natl Acad Sci USA 105: 10513-10518.
23. Lodes M J, Caraballo M, Suciu D, Munro S, Kumar A, et al. (2009) Detection of cancer with serum miRNAs on an oligonucleotide microarray. PLoS ONE 4: e6229.
24. Ng E K O, Chong W W S, Jin H, Lam E K Y, Shin V Y, et al. (2009) Differential expression of microRNAs in plasma of patients with colorectal cancer: a potential marker for colorectal cancer screening. Gut 58: 1375-1381.
25. Huang Z, Huang D, Ni S, Peng Z, Sheng W, et al. (2010) Plasma microRNAs are promising novel biomarkers for early detection of colorectal cancer. Int J Cancer 127: 118-126.
26. Bartels C L, Tsongalis G J (2009) MicroRNAs: novel biomarkers for human cancer. Clin Chem 55: 623-631.
27. Keller A, Leidinger P, Bauer A, Elsharawy A, Haas J, et al. (2011) Toward the blood-borne miRNome of human diseases. Nat Methods 8: 841-843.
28. Cortez M A, Bueso-Ramos C, Ferdin J, Lopez-Berestein G, Sood A K, et al. (2011) MicroRNAs in body fluids—the mix of hormones and biomarkers. Nat Rev Clin Oncol 8: 467-477.
29. Guay C, Regazzi R (2013) Circulating microRNAs as novel biomarkers for diabetes mellitus. Nature reviews Endocrinology.
30. Brase J C, Wuttig D, Kuner R, Siiltmann H (2010) Serum microRNAs as non-invasive biomarkers for cancer. Mol Cancer 9: 306.
31. Kosaka N, Iguchi H, Ochiya T (2010) Circulating microRNA in body fluid: a new potential biomarker for cancer diagnosis and prognosis. Cancer science 101: 2087-2092.
32. Wang K, Zhang S, Weber J, Baxter D, Galas D J (2010) Export of microRNAs and microRNA-protective protein by mammalian cells. Nucl Acids Res 38: 7248-7259.
33. Gibby K A, McDonnell K, Schmidt M O, Wellstein A (2009) A distinct role for secreted fibroblast growth factor-binding proteins in development. Proc Natl Acad Sci USA 106: 8585-8590.

34. Aslam M I, Taylor K, Pringle J H, Jameson J S (2009) MicroRNAs are novel biomarkers of colorectal cancer. Br J Surg 96: 702-710.
35. Cheng H, Zhang L, Cogdell D E, Zheng H, Schetter A J, et al. (2011) Circulating plasma MiR-141 is a novel biomarker for metastatic colorectal cancer and predicts poor prognosis. PLoS ONE 6: e17745.
36. Liao Y, Lonnerdal B (2010) Global microRNA characterization reveals that miR-103 is involved in IGF-1 stimulated mouse intestinal cell proliferation. PLoS ONE 5: e12976.
37. Costa F F, Bischof J M, Vanin E F, Lulla R R, Wang M, et al. (2011) Identification of microRNAs as potential prognostic markers in ependymoma. PLoS ONE 6: e25114.
38. Anwar S L, Albat C, Krech T, Hasemeier B, Schipper E, et al. (2013) Concordant hypermethylation of intergenic microRNA genes in human hepatocellular carcinoma as new diagnostic and prognostic marker. Int J Cancer 133: 660-670.
39. Jamieson N B, Morran D C, Morton J P, Ali A, Dickson E J, et al. (2012) MicroRNA Molecular Profiles Associated with Diagnosis, Clinicopathologic Criteria, and Overall Survival in Patients with Resectable Pancreatic Ductal Adenocarcinoma. Clinical Cancer Research 18: 534-545.
40. Redis R S, Calin S, Yang Y, You M J, Calin G A (2012) Cell-to-cell miRNA transfer: from body homeostasis to therapy. Pharmacol Ther 136: 169-174.
41. Zhang Y, Jia Y, Zheng R, Guo Y, Wang Y, et al. (2010) Plasma MicroRNA-122 as a Biomarker for Viral-, Alcohol-, and Chemical-Related Hepatic Diseases. Clin Chem 56: 1830-1838.
42. Wang K, Zhang S, Marzolf B, Troisch P, Brightman A, et al. (2009) Circulating microRNAs, potential biomarkers for drug-induced liver injury. Proc Natl Acad Sci USA 106: 4402-4407.
43. Cimmino A, Calin G A, Fabbri M, Iorio M V, Ferracin M, et al. (2005) miR-15 and miR-16 induce apoptosis by targeting BCL2. Proc Natl Acad Sci USA 102: 13944-13949.
44. Musumeci M, Coppola V, Addario A, Patrizii M, Maugeri-Saccà M, et al. (2011) Control of tumor and microenvironment cross-talk by miR-15a and miR-16 in colorectal cancer. Oncogene 13: 4231-4242.
45. Spinetti G, Fortunato O, Caporali A, Shantikumar S, Marchetti M, et al. (2013) MicroRNA-15a and microRNA-16 impair human circulating proangiogenic cell functions and are increased in the proangiogenic cells and serum of patients with critical limb ischemia. Circulation Research 112: 335-346.
46. Ng E K O, Li R, Shin V Y, Jin H C, Leung C P H, et al. (2013) Circulating microRNAs as specific biomarkers for breast cancer detection. PLoS ONE 8: e53141.
47. Palma J, Yaddanapudi S C, Pigati L, Havens M A, Jeong S, et al. (2012) MicroRNAs are exported from malignant cells in customized particles. Nucleic Acids Res 40: 9125-9138.

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. A method for predicting recurrence of early stage colorectal cancer in a patient, comprising:
   a) providing a biological material comprising circulating microRNAs from a patient diagnosed with stage 0, stage I or stage II colorectal cancer,
   b) measuring in the biological material the levels of two or more microRNAs selected from: miR-15a, miR-103, miR-148a, miR-320a, miR-451 and miR-596, and
   c) evaluating the measured levels;
   wherein the measured levels are indicative of a risk of recurrence of the cancer.

2. A method comprising:
   a) obtaining a biological material comprising circulating microRNAs from a patient diagnosed with stage 0, stage I, or stage II colorectal cancer, and
   b) detecting in the biological material the levels of two or more microRNAs selected from: miR-15a, miR-103, miR-148a, miR-320a, miR-451, and miR-596.

3. The method of claim 2, wherein said detecting comprises detecting the level of at least one of miR-103 and miR-596.

4. The method of claim 2, wherein said detecting comprises detecting the levels of at least miR-103 and miR-596.

5. The method of claim 2, wherein said detecting consists of detecting the levels of miR-103 and miR-596.

6. The method of claim 2, wherein said detecting comprises detecting the levels of miR-15a, miR-103, miR-148a, miR-320a, miR-451, and miR-596.

7. The method of claim 2, wherein said detecting consists of detecting the levels of miR-15a, miR-103, miR-148a, miR-320a, miR-451, and miR-596.

8. The method of claim 2, wherein the biological material is a biological fluid.

9. The method of claim 8, wherein the biological fluid is selected from: blood plasma, blood serum, whole blood, urine, and feces.

10. The method of claim 2, wherein the biological material is obtained before the cancer is initially surgically resected.

11. The method of claim 2, wherein the biological material is obtained after recovery from surgical resection of the cancer.

12. The method of claim 2, wherein steps (a) and (b) are repeated periodically if the detected microRNA levels are indicative of a low risk of recurrence of the cancer.

13. The method of claim 2, wherein the microRNA levels are measured using quantitative RT-PCR.

14. The method of claim 2, wherein the microRNA levels are measured using hybridization methods.

15. The method of claim 2, wherein the microRNA levels are measured using an array.

16. The method of claim 2 further comprising:
   normalizing the microRNA levels to a control.

17. The method of claim 2 further comprising:
   comparing the microRNA levels to a reference gene signature.

18. The method of claim 2 further comprising:
   providing the levels of said two or more microRNAs in control biological materials obtained from colorectal cancer patients with known recurrence outcome, and hierarchically clustering the microRNA levels detected in the patient's biological material with the levels of said microRNA in the control biological materials.

19. The method of claim 2 further comprising:
selecting an interval for monitoring the patient based on said detecting and
monitoring the patient for changes in the colorectal cancer at the selected interval.

20. The method of claim 2 further comprising:
selecting tests for monitoring the patient based on said detecting and
monitoring the patient using the selected tests for changes in the colorectal cancer.

21. The method of claim 2 further comprising:
selecting a suitable cancer therapeutic based on said detecting and
administering the selected cancer therapeutic to the patient.

22. The method of claim 21, wherein the selected cancer therapeutic comprises chemotherapy, radiation therapy, or therapy targeted to specific pathways known to be important in colorectal cancer or the immune system.

23. A method comprising:
a) obtaining a biological material comprising circulating microRNAs from a patient diagnosed with stage 0, stage I, or stage II colorectal cancer, and
b) detecting in the biological material the levels of two or more microRNAs selected from: miR-15a, miR-103, miR-148a, miR-320a, miR-451, and miR-596, wherein said detecting comprises detecting the level of at least one of miR-103, miR-148a, miR-320a, and miR-596.

* * * * *

UNITED STATES PATENT AND TRADEMARK OFFICE
CERTIFICATE OF CORRECTION

PATENT NO. : 10,351,913 B2
APPLICATION NO. : 15/027284
DATED : July 16, 2019
INVENTOR(S) : Wellstein et al.

Page 1 of 1

It is certified that error appears in the above-identified patent and that said Letters Patent is hereby corrected as shown below:

In the Specification

At Column 1, Line 20, delete "R01CA71508 and R01CA108440, both" and insert in its place --CA017508, CA108440--.

Signed and Sealed this
Tenth Day of October, 2023

Katherine Kelly Vidal
*Director of the United States Patent and Trademark Office*